US008480800B2

(12) United States Patent
Tomlinson et al.

(10) Patent No.: US 8,480,800 B2
(45) Date of Patent: Jul. 9, 2013

(54) AMINOALCOHOL COMPOUNDS, PRECURSORS, AND METHODS OF PREPARATION AND USE

(75) Inventors: Ian A. Tomlinson, Midland, MI (US); Asghar A. Peera, Buffalo Grove, IL (US); George David Green, Cary, IL (US)

(73) Assignee: ANGUS Chemical Company and Dow Global Technologies LLC

( * ) Notice: Subject to any disclaimer, the term of this patent is extended or adjusted under 35 U.S.C. 154(b) by 105 days.

(21) Appl. No.: 12/957,958

(22) Filed: Dec. 1, 2010

(65) Prior Publication Data

US 2011/0146536 A1 Jun. 23, 2011

Related U.S. Application Data

(60) Provisional application No. 61/287,439, filed on Dec. 17, 2009.

(51) Int. Cl.
*C07D 303/36* (2006.01)
*C07D 301/03* (2006.01)
*C07C 213/02* (2006.01)

(52) U.S. Cl.
USPC ...... 106/287.22; 564/506; 564/453; 564/495; 564/448; 106/287.26; 249/551; 249/523

(58) Field of Classification Search
None
See application file for complete search history.

(56) References Cited

U.S. PATENT DOCUMENTS

| 1,962,277 | A | | 6/1934 | Jensch et al. |
| 2,046,720 | A | | 7/1936 | Bottoms |
| 2,205,995 | A | | 6/1940 | Ulrich et al. |
| 4,749,792 | A | * | 6/1988 | Natarajan et al. ............. 546/312 |
| 6,160,022 | A | * | 12/2000 | Bergeron, Jr. ................. 514/674 |

FOREIGN PATENT DOCUMENTS

| WO | 9012782 A1 | 11/1990 |
| WO | 2005056515 A2 | 6/2005 |

OTHER PUBLICATIONS

Vander Werf et al. (Journal of the American chemical Society, 1954, 76, 1231).*
Kullnig et al., The Journal of Biologinal Chemistry, 248(7), 2487, 1973.*
Ando et al., "The electronic delocalization in para-substituted beta-nitrostyrenes probed by resonance Raman spectroscopy and quantum-chemical calculations", Journal of Raman Spectroscopy, 2008, vol. 39, No. 4, pp. 453-459, John Wiley & Sons, Ltd.
Benson et al., "Synthesis and Reactivity of Captodative Diradical Oligomers Incorporating the 3,5,5-Trimethyl-2-oxomorpholin-3-yl (TM-3) Unit", Journal of Organic Chemistry, 1988, vol. 53, pp. 3036-3045, American Chemical Society.
Bergeron et al., "Metabolically Programmed Polyamine Analogue Antidiarrheals", Journal of Medicinal Chemistry, 1996, vol. 39, No. 13, pp. 2461-2471, American Chemical Society.
Dechoux et al., "A simple one-pot preparation of (Z)-cyclopropanes from gamma, delta-ketoalkenes using KOH/DMSO intramolecular alkylation conditions", Tetrahedron Letters, 1993, vol. 34, No. 46, pp. 7405-7408, Pergamon Press Ltd.
Gaudiano et al., "Synthesis of a Capto-Dative Diradical and Its Reversible Oligomerization to Macrocycles of Coronand Structure", Journal of the American Chemical Society, 1984, vol. 106, pp. 7628-7629, American Chemical Society.
Petty, "3-Nitro-3-methyl-1,2-epoxybutane, a Novel alpha-Epoxide Synthesis", Journal of Chemical and Engineering Data, 1968, vol. 13, No. 4, p. 573.
Ponasik et al., "Synthesis of 3-hydroxyspermidine: An unusual polyamine constituent of cytotoxic marine compounds", Tetrahedron Letters, 1995, vol. 36, No. 50, pp. 9109-9112, Elsevier.
Schleppnik et al., "Synthesis and reactions of monsubstituted triptych-boroxazolidines", Journal of Organic Chemistry, 1960, vol. 25, pp. 1378-1386.
Yamamoto et al., "Formation of hydroxynorspermidine from exogenously added 1,3-diaminopropan-2-ol in Vibrio species", Chemical and Pharmaceutical Bulletin, 1989, vol. 37, No. 11, pp. 3139-3141, Pharmaceutical Society of Japan.
International Search Report and Written Opinion for PCT/US2010/058547 dated Mar. 25, 2011.

* cited by examiner

*Primary Examiner* — Yun Qian

(57) ABSTRACT

Provided are aminoalcohol compounds for use as neutralizing agents for paints and coatings. The compounds are of the formula (I):

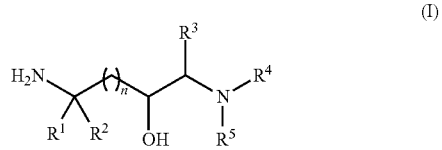

(I)

or salt thereof, wherein $R^1$, $R^2$, $R^3$, $R^4$, $R^5$, and n are as defined herein. Also provided are precursors of the aminoalcohol compounds and processes for making and using them.

14 Claims, No Drawings

AMINOALCOHOL COMPOUNDS, PRECURSORS, AND METHODS OF PREPARATION AND USE

CROSS-REFERENCE TO RELATED APPLICATIONS

This application claims priority to U.S. Provisional Patent Application Ser. No. 61/287,439, filed Dec. 17, 2009, which is incorporated herein by reference in its entirety.

FIELD OF THE INVENTION

The invention relates to aminoalcohol compounds and methods for their preparation. The invention also relates to methods of using such compounds as low odor, low volatile organic content (VOC) additives for paints and coatings.

BACKGROUND OF THE INVENTION

Organic amines are used in aqueous based paints as neutralizing agents. In many geographies, paint manufacturers are facing regulations to reduce the volatile organic content (VOC) of their formulations. Most conventional neutralizing amines are 100% volatile and are therefore VOC contributors. In addition, when used in an otherwise low VOC paint formulation, the odor of such amines is more noticeable.

Ammonia and inorganic hydroxides are potential alternatives for use as neutralizers, that are by definition non-VOC contributors. However, ammonia, while an efficient neutralizer, has a very strong odor and is therefore unsuitable for use in low odor paint. Inorganic hydroxides, such as potassium hydroxide, are undesirable because they often result in coatings with poor scrub resistance.

Accordingly, efficient neutralizing agents, which both exhibit low or no VOC and have very low or no amine odor, would be a significant advance for the paints and coatings industry.

BRIEF SUMMARY OF THE INVENTION

In one aspect, the invention provides low VOC and low odor aminoalcohol compounds that are useful as neutralizing agents for aqueous based paints and coatings. The compounds are of the formula I:

(I)

[Structure: $H_2N$—C($R^1$)($R^2$)—$(CH_2)_n$—CH($R^3$)—CH(OH)—N($R^4$)($R^5$)]

or salt thereof, wherein $R^1$, $R^2$, $R^3$, $R^4$, $R^5$, and n are as defined below.

In another aspect, the invention provides nitroalcohol compounds of the formula II:

(II)

[Structure: $O_2N$—C($R^1$)($R^2$)—$(CH_2)_n$—CH($R^3$)—CH(OH)—N($R^4$)($R^5$)]

wherein $R^1$, $R^2$, $R^3$, $R^4$, $R^5$, and n are as defined below.

In a further aspect, the invention provides nitrated oxirane compounds of the formula IIIA:

(IIIA)

[Structure: oxirane with $R^3$ and $R^1$, $R^2$, $NO_2$ substituents]

wherein $R^1$, $R^2$, and $R^3$ are as defined below.

In a still further aspect, the invention provides an aqueous based paint or coating comprising a compound of formula I as a neutralizing agent.

In a yet further aspect, the invention provides a method for reducing the volatile organic compound content of an aqueous based paint or coating containing a neutralizing agent, a binder, a carrier, and a pigment. The method comprises using, as the neutralizing agent in the paint or coating an effective amount of a compound of formula I.

In another aspect, the invention provides processes for making the compounds of formula I, II, and IIIA.

DETAILED DESCRIPTION OF THE INVENTION

As noted above, in one aspect the invention provides aminoalcohol compounds that are useful as neutralizing agents in aqueous-based paint and coating formulations. Neutralizing agents are included in such formulations to raise the pH to a desired value, typically between about 8 and 10. Most conventional neutralizing agents currently used in the industry are VOC contributors. In addition, when used in an otherwise low VOC formulation, the odor of conventional neutralizing agents is more noticeable.

In contrast, the aminoalcohol compounds of the invention are excellent low odor materials with the benefit of having very low VOC. For instance, 1,1'-(ethane-1,2-diylbis(methylazanediyl))bis(4-amino-4-methylpentan-2-ol), an exemplary compound of the invention, exhibits a VOC contribution that is negligible.

In addition to their excellent low VOC and low odor attributes, the aminoalcohol compounds of the invention impart comparable performance properties to those provided by conventional neutralizing amines. Consequently, the advantages of low odor and low VOC are achieved with the aminoalcohol compounds of the invention, without significant impact on other attributes of the paint or coating. Further, the aminoalcohol compounds of the invention are effective co-dispersants for pigment particles present in paint and coating formulations.

The aminoalcohol compounds of the invention are of the formula I:

(I)

[Structure: $H_2N$—C($R^1$)($R^2$)—$(CH_2)_n$—CH($R^3$)—CH(OH)—N($R^4$)($R^5$)]

or salts thereof, wherein n is 0 or 1;
$R^1$ and $R^2$ are independently H or $C_1$-$C_{10}$ alkyl, or $R^1$ and $R^2$, together with the carbon to which they are attached, form a $C_3$-$C_{12}$ cycloalkyl ring optionally substituted with $C_1$-$C_6$ alkyl (e.g., with 1 or 2 such groups that are independently selected);

$R^3$ is H, $C_1$-$C_{10}$ alkyl, or aryl (e.g., phenyl) optionally substituted with 1 or 2 substituents independently selected from $C_1$-$C_6$ alkyl, aryl, nitro, $C_1$-$C_6$ alkoxy, or ester, provided that when n is 0, $R^3$ is H;

$R^4$ is H, $C_1$-$C_{10}$ alkyl optionally substituted with hydroxy (e.g., 1 or 2 hydroxy, preferably 1 hydroxy), —C($R^6$)($R^7$)$_m$—N($R^8$)($R^9$), or Y, wherein m is an integer from 1 to 6, and $R^6$ and $R^7$ are independently H or $C_1$-$C_{10}$ alkyl;

$R^5$, $R^8$, and $R^9$ are independently H, $C_1$-$C_{10}$ alkyl optionally substituted with hydroxy (e.g., 1 or 2 hydroxy, preferably 1 hydroxy), or Y; and Y is a group of formula:

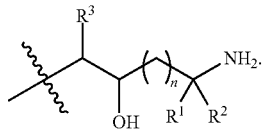

In some embodiments, the aminoalcohols of the invention are compounds of formula I-1, which are compounds of formula I in which $R^4$ is —C($R^6$)($R^7$)$_m$—N($R^8$)($R^9$), $R^5$ and $R^8$ are the same and are H or $C_1$-$C_{10}$ alkyl; and $R^9$ is H. In further embodiments, $R^5$ and $R^8$ are the same and are $C_1$-$C_6$ alkyl, alternatively $C_1$-$C_3$ alkyl, or alternatively methyl. In still further embodiments, $R^6$ and $R^7$ are both hydrogen.

In some embodiments, the aminoalcohols of the invention are compounds of formula I-2, which are compounds of formula I in which $R^4$ is —C($R^6$)($R^7$)$_m$—N($R^8$)($R^9$), $R^5$ and $R^8$ are the same and are H or $C_1$-$C_{10}$ alkyl, and $R^9$ is Y. In further embodiments, $R^5$ and $R^8$ are the same and are $C_1$-$C_6$ alkyl, alternatively $C_1$-$C_3$ alkyl, or alternatively methyl. In still further embodiments, $R^6$ and $R^7$ are both hydrogen.

In some embodiments, the aminoalcohols of the invention are compounds of formula I-3, which are compounds of formula I in which $R^4$ is —C($R^6$)($R^7$)$_m$—N($R^8$)($R^9$), $R^5$ is H or $C_1$-$C_{10}$ alkyl, and $R^8$ and $R^9$ are the same and are both Y. In further embodiments, $R^5$ is $C_1$-$C_6$ alkyl, alternatively $C_1$-$C_3$ alkyl, or alternatively methyl. In still further embodiments, $R^6$ and $R^7$ are both hydrogen.

In some embodiments, the aminoalcohols of the invention are compounds of formula I-4, which are compounds of formula I in which $R^4$ is —C($R^6$)($R^7$)$_m$—N($R^8$)($R^9$), $R^5$, $R^8$ and $R^9$ are the same and are all Y. In further embodiments, $R^6$ and $R^7$ are both hydrogen.

In some embodiments, the aminoalcohols of the invention are compounds of formula I-5, which are compounds of formula I in which $R^4$ is H or $C_1$-$C_{10}$ alkyl optionally substituted with hydroxy, and $R^5$ is $C_1$-$C_{10}$ alkyl substituted with hydroxy (in both cases, preferably 1 hydroxy). In further embodiments, $R^4$ is H. In still further embodiments, $R^4$ is $C_1$-$C_6$ alkyl, alternatively $C_1$-$C_3$ alkyl, alternatively it is ethyl, or alternatively it is methyl. In yet further embodiments, $R^4$ is $C_1$-$C_6$ alkyl substituted with hydroxy (preferably one hydroxy group), alternatively $C_1$-$C_3$ alkyl substituted with hydroxy (preferably one hydroxy group), or alternatively it is 2-hydroxyethyl. In still yet further embodiments, $R^5$ is $C_1$-$C_6$ alkyl substituted with hydroxy (preferably one hydroxy group), alternatively $C_1$-$C_3$ alkyl substituted with hydroxy (preferably one hydroxy group), or alternatively it is 2-hydroxyethyl.

In some embodiments, the aminoalcohols of the invention are compounds of formula I-6, which are compounds of formula I in which $R^4$ is Y, and $R^5$ is $C_1$-$C_{10}$ alkyl substituted with hydroxy (preferably one hydroxy group). In further embodiments, $R^5$ is $C_1$-$C_6$ alkyl substituted with hydroxy (preferably one hydroxy group), alternatively $C_1$-$C_3$ alkyl substituted with hydroxy (preferably one hydroxy group), or alternatively it is 2-hydroxyethyl.

In some embodiments, the aminoalcohols of the invention are compounds of formula I-7, which are compounds of formula I in which $R^4$ and $R^5$ are the same and are both Y.

In some embodiments, the aminoalcohols of the invention are compounds of formula I-8, which are compounds of formulae I, I-1, I-2, I-3, I-4, I-5, I-6, or I-7 in which $R^1$ and $R^2$ are, at all occurrences, either simultaneously hydrogen or simultaneously $C_1$-$C_{10}$ alkyl. In further embodiments, $R^1$ and $R^2$ are at all occurrences $C_1$-$C_6$ alkyl, alternatively $C_1$-$C_3$ alkyl, or alternatively methyl.

In some embodiments, the aminoalcohols of the invention are compounds of formula I-9, which are compounds of formulae I, I-1, I-2, I-3, I-4, I-5, I-6, or I-7 in which $R^1$ and $R^2$, together with the carbon to which they are attached, form a $C_3$-$C_{12}$ cycloalkyl ring. In further embodiments, $R^1$ and $R^2$, together with the carbon to which they are attached, form a cyclohexyl ring.

In some embodiments, the aminoalcohols of the invention are compounds of formula I-10, which are compounds of formulae I, I-1, I-2, I-3, I-4, I-5, I-6, I-7, I-8, or I-9 in which $R^3$ at all occurrences is H.

In some embodiments, the aminoalcohols are compounds of formula I-11, which are compounds of formulae I, I-1, I-2, I-3, I-4, I-5, I-6, I-7, I-8, I-9, or I-10 in which n at all occurrences is 1.

In some embodiments, the aminoalcohols are compounds of formula I-12, which are compounds of formulae I, I-1, I-2, I-3, I-4, I-5, I-6, I-7, I-8, I-9, or I-10 in which n at all occurrences is 0 (i.e., the groups between the parentheses are absent).

In some embodiments, the aminoalcohols are compounds as shown in Table 1.

TABLE 1

| Name | Structure |
|---|---|
| 1,1'-(ethane-1,2-diylbis(methylazanediyl))bis(4-amino-4-methylpentan-2-ol) | 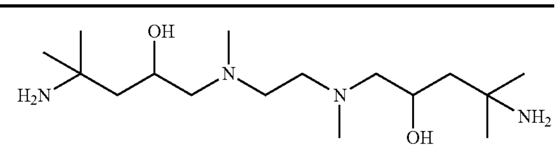 |

TABLE 1-continued

| Name | Structure |
| --- | --- |
| 1,1'-(2-hydroxyethylazanediyl)bis(4-amino-4-methylpentan-2-ol) | 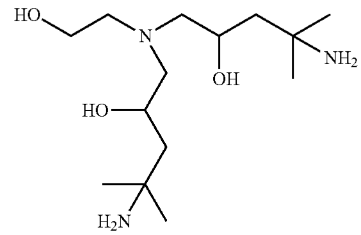 |
| 3,3'-(ethane-1,2-diylbis(methylazanediyl))bis(1-(1-aminocyclohexyl)propan-2-ol) | 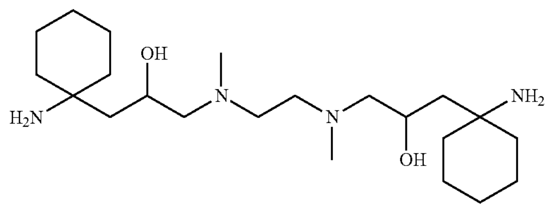 [SMILES: CN(CCN(C)CC(O)CC1([N+](=O)[O-])CCCCC1)CC(O)CC1([N+](=O)[O-])CCCCC1] |
| 1-(1-aminocyclohexyl)-3-((2-hydroxyethyl)(methyl)amino)propan-2-ol | 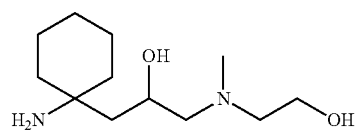 [SMILES: CN(CCO)CC(O)CC1([N+](=O)[O-])CCCCC1] |
| 4-amino-1-((2-hydroxyethyl)(methyl)amino)-4-methylpentan-2-ol | 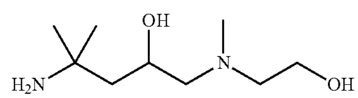 |
| 2,2'-(3-(1-aminocyclohexyl)-2-hydroxypropylazanediyl)diethanol | 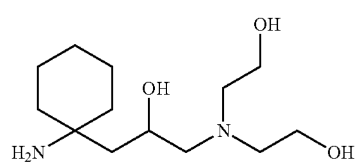 [SMILES: O=[N+]([O-])C1(CC(O)CN(CCO)CCO)CCCCC1] |
| 2,2'-(4-amino-2-hydroxy-4-methylpentylazanediyl)diethanol | 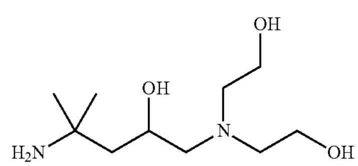 [SMILES: CC(C)(CC(O)CN(CCO)CCO)[N+](=O)[O-]] |
| 4-amino-1-(2-hydroxyethylamino)-4-methylpentan-2-ol | 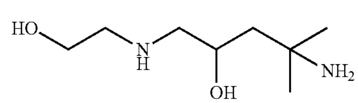 |
| 4-amino-4-methyl-1-(methyl(2-(methylamino)ethyl)amino)pentan-2-ol | 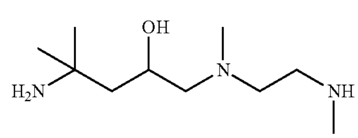 |
| 4-amino-1-(1-hydroxy-2-methylpropan-2-ylamino)-4-methylpentan-2-ol | 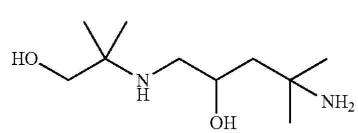 |

TABLE 1-continued

| Name | Structure |
|---|---|
| 1,1′,1″,1‴-(hexane-1,6-diylbis(azanetriyl))tetrakis(4-amino-4-methylpentan-2-ol) | 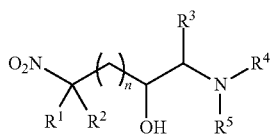 |

The compounds of formula I may be in the form of acid salts (e.g., following their use as paint and coating neutralizing agents as described below). Suitable salts include, but are not limited to, hydrochloric acid, boric acid, lactic acid, pelargonic acid, nonanoic acid, neodecanoic acid, sebacic acid, azelaic acid, citric acid, benzoic acid, undecylenic acid, lauric acid, myristic acid, stearic acid, oleic acid, tall oil fatty acid, ethylenediaminetetraacetic acid and like materials.

In another aspect, the invention provides nitroalcohol compounds from which the aminoalcohol compounds of formula I may be prepared (using the methods described below). The nitroalcohol compounds are of the formula II:

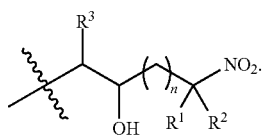
(II)

wherein $R^1$ and $R^2$ are independently H or $C_1$-$C_{10}$ alkyl, or $R^1$ and $R^2$, together with the carbon to which they are attached, form a $C_3$-$C_{12}$ cycloalkyl ring optionally substituted with $C_1$-$C_6$ alkyl (e.g., with 1 or 2 such groups that are independently selected);

$R^3$ is H, $C_1$-$C_{10}$ alkyl, or aryl, wherein aryl is optionally substituted with 1 or 2 substituents independently selected from $C_1$-$C_6$ alkyl, aryl, nitro, $C_1$-$C_6$ alkoxy, or ester, provided that when n is 0, $R^3$ is H;

$R^4$ is H, $C_1$-$C_{10}$ alkyl optionally substituted with hydroxy (e.g., 1 or 2 hydroxy, preferably 1 hydroxy), —$C(R^6)(R^7))_m$—$N(R^{8'})(R^{9'})$, or Y', wherein m is an integer from 1 to 6, and $R^6$ and $R^7$ are independently H or $C_1$-$C_{10}$ alkyl;

$R^5$, $R^8$, and $R^9$ are independently H, $C_1$-$C_{10}$ alkyl optionally substituted with hydroxy (e.g., 1 or 2 hydroxy, preferably 1 hydroxy), or Y'; and Y' is a group of formula:

In some embodiments, the nitroalcohol compounds of the invention are compounds of formula II-1, which are compounds of formula II in which $R^4$ is —$(C(R^6)(R^7))_m$—$N(R^8)(R^9)$, $R^5$ and $R^8$ are the same and are H or $C_1$-$C_{10}$ alkyl; and $R^9$ is H. In further embodiments, $R^5$ and $R^8$ are the same and are $C_1$-$C_6$ alkyl, alternatively $C_1$-$C_3$ alkyl, or alternatively methyl. In still further embodiments, $R^6$ and $R^7$ are both hydrogen.

In some embodiments, the nitroalcohol compounds of the invention are compounds of formula II-2, which are compounds of formula II in which $R^4$ is —$(C(R^6)(R^7))_m$—$N(R^8)(R^9)$, $R^5$ and $R^8$ are the same and are H or $C_1$-$C_{10}$ alkyl, and $R^9$ is Y'. In further embodiments, $R^5$ and $R^8$ are the same and are $C_1$-$C_6$ alkyl, alternatively $C_1$-$C_3$ alkyl, or alternatively methyl. In still further embodiments, $R^6$ and $R^7$ are both hydrogen.

In some embodiments, the nitroalcohol compounds of the invention are compounds of formula II-3, which are compounds of formula II in which $R^4$ is —$(C(R^6)(R^7))_m$—$N(R^8)(R^9)$, $R^5$ is H or $C_1$-$C_{10}$ alkyl, and $R^8$ and $R^9$ are the same and are both Y'. In further embodiments, $R^5$ is $C_1$-$C_6$ alkyl, alternatively $C_1$-$C_3$ alkyl, or alternatively methyl. In still further embodiments, $R^6$ and $R^7$ are both hydrogen.

In some embodiments, the nitroalcohol compounds of the invention are compounds of formula II-4, which are compounds of formula II in which $R^4$ is —$(C(R^6)(R^7))_m$—$N(R^8)(R^9)$, $R^5$, $R^8$ and $R^9$ are the same and are all Y'. In further embodiments, $R^6$ and $R^7$ are both hydrogen.

In some embodiments, the nitroalcohol compounds of the invention are compounds of formula II-5, which are compounds of formula II in which $R^4$ is H or $C_1$-$C_{10}$ alkyl optionally substituted with hydroxy, and $R^5$ is $C_1$-$C_{10}$ alkyl substituted with hydroxy (in both cases, preferably 1 hydroxy). In further embodiments, $R^4$ is H. In still further embodiments, $R^4$ is $C_1$-$C_6$ alkyl, alternatively $C_1$-$C_3$ alkyl, alternatively it is ethyl, or alternatively it is methyl. In yet further embodiments, $R^4$ is $C_1$-$C_6$ alkyl substituted with hydroxy (preferably one hydroxy group), alternatively $C_1$-$C_3$ alkyl substituted with hydroxy (preferably one hydroxy group), or alternatively it is 2-hydroxyethyl. In still yet further embodiments, $R^5$ is $C_1$-$C_6$ alkyl substituted with hydroxy (preferably one hydroxy group), alternatively $C_1$-$C_3$ alkyl substituted with hydroxy (preferably one hydroxy group), or alternatively it is 2-hydroxyethyl.

In some embodiments, the nitroalcohol compounds of the invention are compounds of formula II-6, which are compounds of formula II in which $R^4$ is Y', and $R^5$ is $C_1$-$C_{10}$ alkyl substituted with hydroxy (preferably one hydroxy group). In further embodiments, $R^5$ is $C_1$-$C_6$ alkyl substituted with hydroxy (preferably one hydroxy group), alternatively $C_1$-$C_3$ alkyl substituted with hydroxy (preferably one hydroxy group), or alternatively it is 2-hydroxyethyl.

In some embodiments, the nitroalcohol compounds of the invention are compounds of formula II-7, which are compounds of formula II in which $R^4$ and $R^5$ are the same and are both Y'.

In some embodiments, the nitroalcohol compounds of the invention are compounds of formula II-8, which are compounds of formulae II, II-1, II-2, II-3, II-4, II-5, II-6, or II-7 in which $R^1$ and $R^2$ are, at all occurrences, either simultaneously hydrogen or simultaneously $C_1$-$C_{10}$ alkyl. In further embodiments, $R^1$ and $R^2$ are at all occurrences $C_1$-$C_6$ alkyl, alternatively $C_1$-$C_3$ alkyl, or alternatively methyl.

In some embodiments, the nitroalcohol compounds of the invention are compounds of formula II-9, which are compounds of formulae II, II-1, II-2, II-3, II-4, II-5, II-6, or II-7 in which $R^1$ and $R^2$, together with the carbon to which they are attached, form a $C_3$-$C_{12}$ cycloalkyl ring. In further embodiments, $R^1$ and $R^2$, together with the carbon to which they are attached, form a cyclohexyl ring.

In some embodiments, the nitroalcohol compounds of the invention are compounds of formula II-10, which are compounds of formulae II, II-1, II-2, II-3, II-4, II-5, II-6, II-7, II-8, or II-9 in which $R^3$ at all occurrences is H.

In some embodiments, the nitroalcohol compounds are compounds of formula II-11, which are compounds of formulae II, II-1, II-2, II-3, II-4, II-5, II-6, II-7, II-8, II-9, or II-10 in which n at all occurrences is 1.

In some embodiments, the nitroalcohol compounds are compounds of formula II-12, which are compounds of formulae II, II-1, II-2, II-3, II-4, II-5, II-6, II-7, II-8, II-9, or II-10 in which n at all occurrences is 0 (i.e., the groups between the parentheses are absent).

In some embodiments, the nitroalcohol compounds are as shown in Table 2.

TABLE 2

| Name | Structure |
|---|---|
| 1,1'-(ethane-1,2-diylbis(methylazanediyl))bis(4-methyl-4-nitropentan-2-ol) | 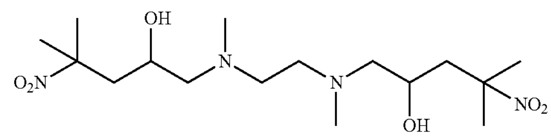 |
| 1,1'-(2-hydroxyethylazanediyl)bis(4-methyl-4-nitropentan-2-ol) | 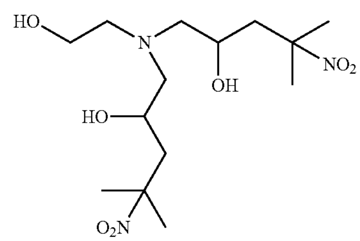 |
| 3,3'-(ethane-1,2-diylbis(methylazanediyl))bis(1-(1-nitrocyclohexyl)propan-2-ol) | 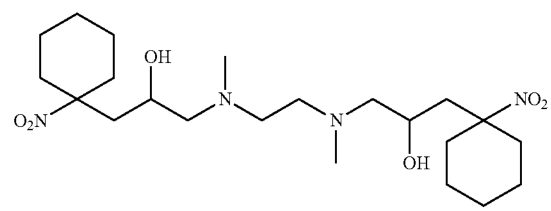 |
| 1-((2-hydroxyethyl)(methyl)amino)-3-(1-nitrocyclohexyl)propan-2-ol | 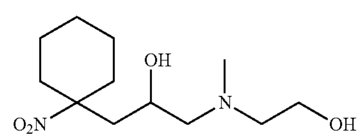 |
| 1-((2-hydroxyethyl)(methyl)amino)-4-methyl-4-nitropentan-2-ol | |
| 2,2'-(2-hydroxy-3-(1-nitrocyclohexyl)propylazanediyl)diethanol | 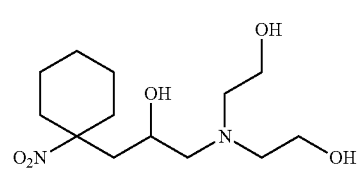 |

TABLE 2-continued

| Name | Structure |
|---|---|
| 2,2'-(2-hydroxy-4-methyl-4-nitropentylazanediyl)diethanol | 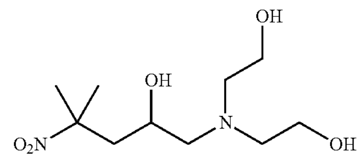 |
| 4-methyl-1-(methyl(2-(methylamino)ethyl)amino)-4-nitropentan-2-ol | 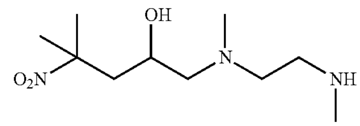 [SMILES: CNCCN(C)CC(O)CC(C)(C)[N+](=O)[O-]] |
| 1-(2-hydroxyethylamino)-4-methyl-4-nitropentan-2-ol | 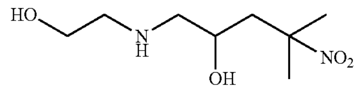 |
| 1-(1-hydroxy-2-methylpropan-2-ylamino)-4-methyl-4-nitropentan-2-ol | 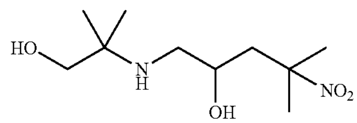 [SMILES: CC(C)(CO)NCC(O)CC(C)(C)[N+](=O)[O-]] |
| 1,1'-((6-(bis(2-hydroxy-4-methyl-4-nitropentyl)amino)hexyl)azanediyl)bis(4-methyl-4-nitropentan-2-ol) | 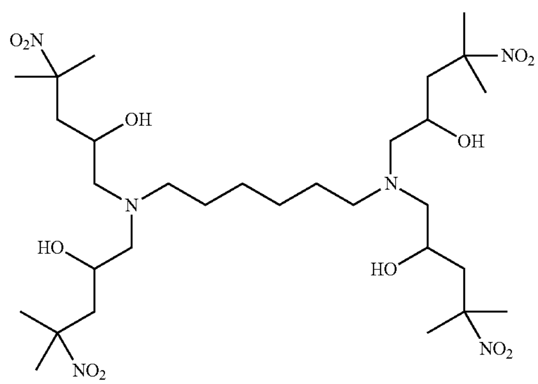 [SMILES: CC(C)(CC(O)CN(CCCCCCN(CC(O)CC(C)(C)[N+](=O)[O-])CC(O)CC(C)(C)[N+](=O)[O-])CC(O)CC(C)(C)[N+](=O)[O-])[N+](=O)[O-]] |

In a further aspect, the invention provides nitrated oxirane compounds from which the aminoalcohol compounds of formula I and nitroalcohol compounds of formula II may be prepared (using the methods described below). The nitrated oxirane compounds are of the formula IIIA:

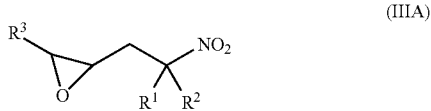

(IIIA)

wherein $R^1$ and $R^2$ are independently hydrogen or $C_1$-$C_{10}$ alkyl, or $R^1$ and $R^2$, together with the carbon to which they are attached, form a $C_3$-$C_{12}$ cycloalkyl ring optionally substituted with $C_1$-$C_6$ alkyl; and $R^3$ is H, $C_1$-$C_{10}$ alkyl, or phenyl.

In some embodiments, the nitrated oxiranes of the invention are compounds of formula IIIA-1, which are compounds of formula IIIA in which $R^1$ and $R^2$ are simultaneously hydrogen or simultaneously $C_1$-$C_{10}$ alkyl. In further embodiments, $R^1$ and $R^2$ are simultaneously $C_1$-$C_6$ alkyl, alternatively $C_1$-$C_3$ alkyl, or alternatively methyl.

In some embodiments, the nitrated oxiranes of the invention are compounds of formula IIIA-2, which are compounds of formula IIIA in which $R^1$ and $R^2$ together with the carbon to which they are attached form a $C_3$-$C_{12}$ cycloalkyl ring optionally substituted with $C_1$-$C_6$ alkyl. In further embodiments, $R^1$ and $R^2$ and the carbon to which they are attached form a cyclohexyl ring.

In some embodiments, the nitrated oxiranes are compounds of formula IIIA-3, which are compounds of formula IIIA, IIIA-1, or IIIA-2 in which $R^3$ is H.

In some embodiments, the nitrated oxirane compound is 2-(2-methyl-2-nitropropyl)oxirane. In some embodiments, the nitrated oxirane compound is 2-((1-nitrocyclohexyl)methyl)oxirane.

In a further aspect, the invention provides an aqueous based paint or coating in which a compound of formula I is present as a neutralizing agent. The paint or coating is used to provide a protective and/or decorative barrier for residential and industrial surfaces, such as for floors, automobiles, exteriors and interiors of houses, and other buildings. According to this aspect of the invention, the paint or coating formulation, in addition to comprising a neutralizing agent, also comprises a binder, a pigment, and a carrier.

Pigments are included to provide hiding power and the desired color to the final coated material and may also be used to provide bulk to the paint or coating. While multiple pigments may be present in end-use paints or coatings, sometimes only white pigment, such as titanium oxide, perhaps in combination with extender pigments such as calcium carbonate and/or kaolin clay, is added in the early stages of the formation of the formulation. Any other desired pigments of various colors (including more white pigment) can optionally be added at the later stages of, or after, the formulation is completed.

Pigments may be organic or inorganic. Examples of pigments can include, but are not limited to, titanium dioxide, kaolin clay, calcined kaolin clay, carbon black, iron oxide black, iron oxide yellow, iron oxide red, iron oxide brown, organic red pigments, including quinacridone red and metallized and non-metallized azo reds (e.g., lithols, lithol rubine, toluidine red, naphthol red), phthalocyanine blue, phthalocyanine green, mono- or di-arylide yellow, benzimidazolone yellow, heterocyclic yellow, quinacridone magenta, quinacridone violet, and the like, and any combination thereof.

Binders are included in the paint and coating formulations to provide a network in which the pigment particles are dispersed and suspended. Binders bind the pigment particles together and provide integrity and adhesion for the paint or coating film. Generally, there are two classes of binders: latex binders are used in aqueous based formulations, and alkyd-based binders are used in non-aqueous formulations, ultimately resulting in latex paints and coatings and alkyd paints and coatings, respectively.

In latex based paint and coating formulations, the binders are typically prepared by free radical initiated aqueous emulsion polymerization of a monomer mixture containing alkyl acrylate (methyl acrylate, ethyl acrylate, butyl acrylate and/or 2-ethylhexylacrylate), alkyl methacrylate, vinyl alcohol/acetate, styrene, and/or acrylonitrile and ethylene type monomers. Preferred binders include acrylic, vinyl acrylic, styrenated-acrylic, or vinyl acetate ethylene based materials. The amount of the binder in the formulations of the invention can be the amount conventionally used in paint and coating formulations, which can vary widely due to the desired gloss/sheen range, and also the solids concentration, of a specific paint formulation. By way of non-limiting examples, the amount of binder solids may be from about 2% to about 75%, alternatively from about 5% to about 65%, or alternatively from about 20% to about 55%, by weight based on the total weight of the formulation.

The formulations also contain a carrier in which the formulation ingredients are dissolved, dispersed, and/or suspended. In the aqueous based formulations of the invention, the carrier is usually water, although other water-based solutions such as water-alcohol mixtures and the like may be used. The aqueous carrier generally makes up the balance of the formulation, after all the other ingredients have been accounted for.

Other additives may be included in the paint and coating formulations besides the neutralizing agents, pigments, binders, and carriers discussed above. These include, but are not limited to, leveling agents and surfactants, thickeners, rheology modifiers, co-solvents such as glycols, including propylene glycol or ethylene glycol, corrosion inhibitors, defoamers, co-dispersants, additional aminoalcohol compounds, and biocides.

The paint and coating formulations of the invention may be manufactured by conventional paint manufacturing techniques, which are well known to those skilled in the art. Typically, the formulations are manufactured by a two-step process. First, a dispersion phase, commonly referred to as the grind phase, is prepared by mixing the dry pigments with other grind phase components, including most other solid powder formulation materials, under constant high shear agitation to provide a high viscosity and high solids mixture. This part of the process is designed to effectively wet and dis-agglomerate the dry pigments and stabilize them in an aqueous dispersion.

The second step of the paint manufacturing process is commonly referred to as the letdown or thindown phase, because the viscous grind is diluted with the remaining formulation components, which are generally less viscous than the grind mix. Typically, the binders, any predispersed pigments, and any other paint materials that only require mixing and perhaps moderate shear, are incorporated during the letdown phase. The letdown phase may be done either by sequentially adding the letdown components into a vessel containing the grind mix, or by adding the grind mix into a vessel containing a premix of the latex resins and other letdown components, followed by sequential addition of the final letdown components. In either case, constant agitation is needed, although application of high shear is not required. The neutralizing agent compounds of the invention are typically added to the formulation at one or more of three different places in the manufacturing process: to the pigment dispersion, to the binder dispersion, and/or in a final addition to the paint formulation. The amount used is determined based on the desired pH of the formulation. Typically, an amount of the compound is added so as to provide a final pH in the range of about 8 and 10, more preferably about 8.5 to 9.5.

In a further aspect, the invention provides a method for reducing the volatile organic compound content of an aqueous based paint or coating that contains a neutralizing agent, a binder, a carrier, and a pigment. The method comprises using as the neutralizing agent an effective amount of a compound for formula I. As noted above, an effective amount is the quantity required to provide a pH of about 8 to 10, preferably 8.5 to 9.5, in the paint or coating formulation.

The invention further provides processes for making the aminoalcohol compounds described above, as well as their precursor compounds. Scheme I illustrates the processes. $R^1$, $R^2$, $R^3$, $R^4$, $R^5$, $R^6$, X, m, and n in Scheme I are the same as defined above for compounds of formula I, II, and IIIA, including all embodiments thereof.

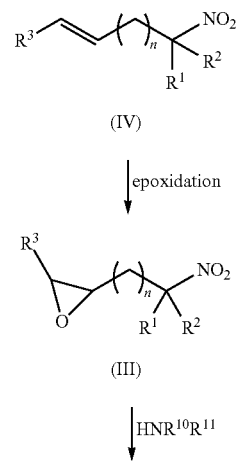

SCHEME I

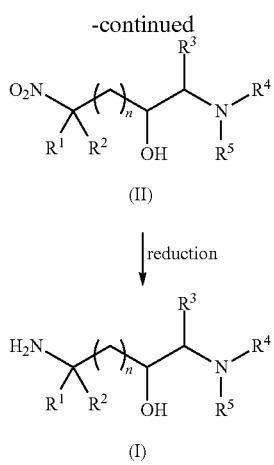

Nitrated alkenes of formula IV are commercially available or can be readily prepared by those skilled in the art using well known literature techniques. Nitroalkyl-oxirane compounds of formula III, including for instance compounds of formula IIIA shown above, may be prepared by the epoxidation of the formula IV nitrated alkene by an epoxidation reaction. Any epoxidation reagent capable of oxidizing an alkene to an epoxy group may be used. Typical epoxidation reagents include m-CPBA, Oxone, and hydrogen peroxide. A preferred epoxidation reagent is meta-chloroperoxybenzoic acid (m-CPBA). Typically, the reaction is conducted under inert atmosphere and in the presence of a solvent, such as methylene chloride. An excess of the epoxidation reagent may be used. The reaction may be conducted at a temperature between about 0 and about 55° C., preferably 0 to 45° C. Following sufficient time for reaction to occur, e.g., 1 to 6 hours, the desired product may be isolated or purified using known techniques.

By way of example of the epoxidation reaction, nitrated oxiranes of formula IIIA may be prepared by epoxidation of a nitrated alkene compound of formula IVA:

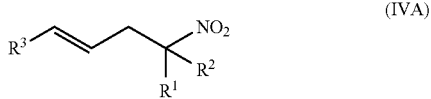

using the process described above. Preferably, the reaction is conducted in methylene chloride at a temperature between 0 and 45° C. Preferably, m-CPBA is used as the epoxidation reagent.

The process for preparing the nitroalcohol compound of formula II comprises combining a nitroalkyloxirane compound of formula III with an amine compound. The amine compound may have the formula $HNR^{10}R^{11}$, wherein:

$R^{11}$ is H, or $C_1$-$C_{10}$ alkyl optionally substituted with hydroxy; and $R^{10}$ is H, $C_1$-$C_{10}$ alkyl optionally substituted with hydroxy, or $—(C(R^6)(R^7))_m—N(R^{12})(R^{13})$, wherein m is an integer from 1 to 6, and $R^6$ and $R^7$ are independently H or $C_1$-$C_{10}$ alkyl, and $R^{12}$ and $R^{13}$ are independently H or $C_1$-$C_{10}$ alkyl optionally substituted with hydroxy.

In some embodiments, $R^{10}$ in the amine is H and $R^{11}$ is $C_1$-$C_{10}$ alkyl substituted with hydroxy (preferably one hydroxy).

In some embodiments, $R^{10}$ in the amine is $C_1$-$C_{10}$ alkyl and $R^{11}$ is $—(C(R^6)(R^7))_m—N(R^{12})(R^{13})$. In further embodiments, $R^6$, $R^7$, and $R^{12}$ are H, and $R^{13}$ is $C_1$-$C_{10}$ alkyl.

In some embodiments, the amine of formula $HNR^{10}R^{11}$ is N,N'-dimethylethane-1,2-diamine, ethanolamine, 2-(methylamino)ethanol, ethane-1,2-diamine, bis(hydroxy-ethyl)amine, 2-amino-2-methylpropan-1-ol, ammonia, or hexamethylenediamine.

The number of molar equivalents of the nitroalkyloxirane of formula III relative to the amine compound may be selected by a person of ordinary skill in the art, based on the final product compound that is desired. In some embodiments, at least one molar equivalent of the nitroalkyloxirane is used, in some embodiments, more than one molar equivalent is used. In further embodiments, at least 2 molar equivalents, alternatively at least 3 molar equivalents, or alternatively at least 4 molar of the equivalents of the nitroalkyloxirane relative to the amine compound are used.

The reaction may be carried out at elevated temperature, such as at 50-80° C., and for sufficient time for the combination to occur, such as 1 to 12 hours. A solvent may optionally be used. Following reaction, the nitroalcohol compounds of formula II may be purified or isolated from the reaction mixture using techniques well known to those skilled in the art. Alternatively, the product may be used without isolation and/or purification. In some embodiments, the product is a mixture of nitroalcohol compounds of formula II.

Nitroalcohol compounds of formula II may be converted to aminoalcohols of formula I via reduction using any reagent capable of reducing aliphatic nitro groups. Examples of such reducing agents include hydrogen gas in combination with a catalyst, for example, Raney nickel or a platinum or palladium based catalyst (Pt or Pd in elemental form or as oxides, with or without supports, e.g., carbon); and other reducing agents including metal/acid combinations, e.g., iron/acetic acid; aluminum hydrides, e.g., VITRIDE. Preferred reducing agents include hydrogen gas in combination with any of the following catalysts: Raney nickel, platinum, or palladium. Conditions for hydrogenation of nitro groups are well known, e.g., a temperature range of about 20-80° C. at a pressure of about 100-1000 psi (690 kPa-6900 kPa) are typical, although these can be readily adjusted by one skilled in the art. In some embodiments, the reduced product is a mixture of aminoalcohols of formula I.

The aminoalcohol compounds of the invention are useful as neutralizing agents in aqueous-based paint and coating formulations. The compounds are excellent low odor materials with the benefit of having very low VOC. Advantageously, the compounds of the invention impart comparable performance properties to those provided by conventional neutralizing amines when used in paints and coatings. Consequently, the advantages of low odor and low VOC are achieved with the aminoalcohol compounds of the invention, without significant impact on other attributes of the paint or coating. Further, the aminoalcohol compounds of the invention are effective co-dispersants for pigment particles present in paint and coating formulations.

The term "alkyl" as used herein, means a straight or branched chain hydrocarbon containing the indicated number of carbon atoms. If no number is indicated, then alkyl contains from 1 to 10 carbon atoms, preferably 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, and n-hexyl. By "optionally substituted with hydroxy" is meant that 1, 2, or 3 hydrogens of the alkyl may be replaced with OH groups. The hydroxy groups may be present on internal or terminal carbons, or both. Preferred alkyl that are substituted with hydroxy contain one such hydroxy. Further preferably, the hydroxy is on a terminal carbon.

The term "cycloalkyl" as employed herein includes saturated and partially unsaturated cyclic hydrocarbon groups having 3 to 12 carbons, preferably 5 to 8 carbons. Preferred cycloalkyl groups include, without limitation, cyclopropyl, cyclobutyl, cyclopentyl, cyclopentenyl, cyclohexyl, cyclohexenyl, cycloheptyl, and cyclooctyl.

The term "aryl" means a $C_6$-$C_{12}$ aromatic moiety comprising one to three aromatic rings. Preferably, the aryl group is a $C_6$-$C_{10}$ aryl group. Preferred aryl groups include, without limitation, phenyl, biphenyl, naphthyl, anthracenyl, and fluorenyl.

Unless otherwise indicated, ratios, percentages, parts, and the like used herein are by weight.

The following examples are illustrative of the invention but are not intended to limit its scope.

EXAMPLES

Example 1

Preparation of 4-methyl-4-nitropent-1-ene

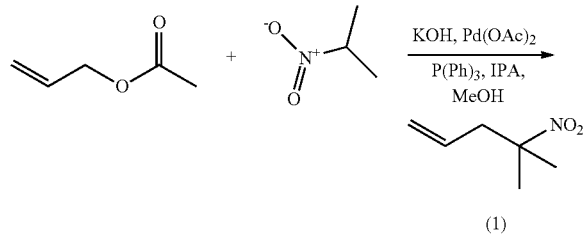

(1)

A 3 neck 500 mL round bottom flask equipped with dropping funnel, temperature controller, nitrogen outlet, stir bar and condenser is charged with 17.3 g (0.309 mols) of potassium hydroxide (KOH), 50 mL of methanol and 150 mL of isopropanol. The addition takes place at room temperature, however, while the base is dissolving in the solvent there is a 20° C. increase in temperature. The base solution is let to stir under nitrogen for 20 minutes and during that period, the temperature of the flask goes down to 35° C. To the above base solution, 25 g of 2-nitropropane ("2-NP") (0.281 mols) is added slowly with vigorous stiffing of the mixture. The mixture is stirred for 10 minutes and palladium acetate (0.56 mmol)/triphenyl phosphine (1.7 mmol) added as catalyst. The resulting yellow solution is stirred under nitrogen for another 5 minutes and 30.9 g of allyl acetate added drop-wise to the mixture via the dropping funnel. During the addition of the acetate, the reaction mixture turns dark and cloudy, followed by dark brown to clear orange and finally clear yellow upon completion of addition. During the addition, the temperature rises to about 60° C. At this point, heat is switched on and the mixture stirred for 6 h at 60° C. followed by overnight stiffing at room temperature. The next day the mixture is heated again to 60° C. followed by room temperature stirring overnight. The total reaction time is 48 h.

After the reaction is complete, the contents of the flask are poured into a separatory funnel containing 300 mL of water. The organic layer is extracted with pentane (3×150 mL) and dried under $MgSO_4$. Excess solvent is stripped off under a rotary evaporator and 20 g of yellow solution obtained. The solution is purified by vacuum distillation at 25 mmHg, which results in 17 g (53%) of 4-methyl-4-nitropent-1-ene as colorless solution at 96-98% purity. The retention time of the alkene on the GC is 7.4 minutes. GC/MS analysis shows $[MH]^+$ m/z 83. $^1$H NMR ($CDCl_3$): $\partial$ 0.91 (s, 6 H), $\partial$ 2.63 (d, 2 H), $\partial$ 5.07-5.17 (m, 2 H) and $\partial$ 5.59 (m, 1 H). $^{13}$C NMR ($CDCl_3$): $\partial$ 25.3, 44.8, 87.6, 120 and 131 ppm.

Example 2

Preparation of 2-(2-methyl-2-nitropropyl)oxirane

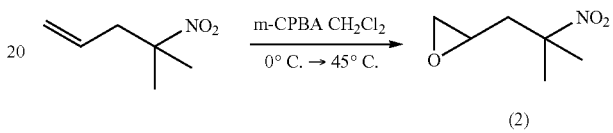

(2)

A 3 neck 100 mL round bottom flask equipped with dropping funnel, temperature controller, nitrogen outlet, stir bar and condenser is charged with 1.54 g (11 mmol) of alkene and 15 mL of $CH_2Cl_2$. To the solution, 2.68 g (16 mmol) of mCPBA dissolved in 25 mL $CH_2Cl_2$ is added slowly. After complete addition, the reaction is refluxed for 6 hrs and progress of the reaction monitored by GC. After 6 h, there is about 80% conversion to the epoxide. The reaction is cooled to room temperature and the solid mCPBA that crashes out of solution removed by gravity filtration. The yellow filtrate is placed in the flask again and 0.3 mol equivalent of the mCPBA in $CH_2Cl_2$ solution is added to the flask. The mixture is refluxed again for 2 hrs and at this point, resulting in 100% conversion to the epoxide. The reaction mixture is cooled to room temperature and excess mCPBA removed by gravity filtration. The organic layer is washed with 10% $Na_2CO_3$ (3×15 mL) followed by brine (3×15 mL). The organic layer is dried under $MgSO_4$ and excess solvent stripped off under rotary evaporator. This affords 0.73 g (50%) of pure epoxide. The retention time of the epoxide on the GC is 11.0 minutes. $^1$H NMR ($CDCl_3$): $\partial$ 1.62 (s, 6 H), $\partial$ 1.96 (m, 2 H), $\partial$ 2.32 (m, 1 H), $\partial$ 2.53 (m, 1 H) and $\partial$ 2.97 (m, 1 H). $^{13}$C NMR ($CDCl_3$): $\partial$ 25.3, 26.9, 43.3, 46.0, 47.9 and 87.0 ppm.

Example 3

Reaction of 2-(2-methyl-2-nitropropyl)oxirane with N,N'-DMEDA (3)

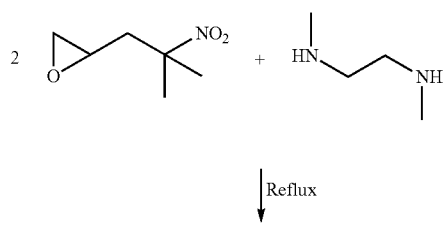

↓ Reflux

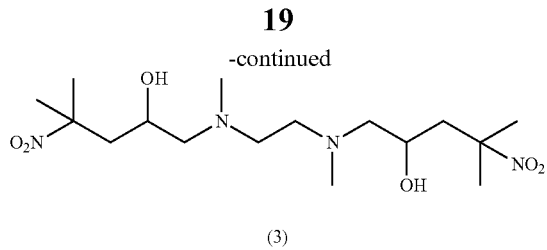

(3)

A one neck 100 mL round bottom flask equipped with a stir bar, condenser and nitrogen outlet is charged with 16.6 g (0.114 mols) of 2-(2-methyl-2-nitropropyl)oxirane and 5.0 g (0.057 mols) of N,N'-dimethylethane-1,2-diamine. The reaction mixture is stirred at room temperature for 30 minutes followed by heating at 60° C. for 2 h and at 80° C. for 6 h. The yellow color oxirane turns to dark orange and the resulting product has high viscosity. GC analysis of the resulting mixture shows the starting materials are consumed during the 6 h reaction and there is only one product present with retention time of 20.1 minutes. This new peak corresponds to the mono adduct. The molecular weight of the bis adduct is too large to elute in GC. Compound 3 is characterized by NMR. $^{13}$C NMR (CDCl$_3$): ∂ 25.6, 25.7, 43.2, 44.6, 53.9, 63.7, 64.2 and 87.7 ppm. The extra peaks on the spectra corresponds to the mono adduct formed as an intermediate during the reaction.

Example 4

Reaction of 2-(2-methyl-2-nitropropyl)oxirane with ethanolamine (4)

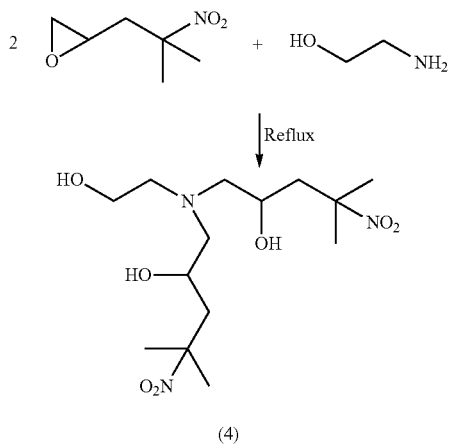

(4)

A one neck 100 mL round bottom flask equipped with a stir bar, condenser and nitrogen outlet is charged with 20 g (0.18 mols) of 2-(2-methyl-2-nitropropyl)oxirane and 5.7 g (0.09 mols) of ethanolamine. The reaction mixture is stirred at room temperature for 30 minutes followed by heating at 60° C. for 2 h and at 80° C. for 8 h. The yellow color oxirane turns to dark orange and the resulting product has high viscosity. GC analysis of the resulting mixture shows the starting materials are consumed during the 8 h reaction and there is only one product present with retention time of 20.4 minutes. This new peak corresponded to the mono adduct. The molecular weight of the bis adduct is too large to elute in GC. Compound 4 is characterized by NMR. $^{13}$C NMR (CDCl$_3$): ∂ 25.1, 25.7, 44.0, 50.2, 54.5, 59.9, 65.0 and 86.6 ppm. The extra peaks on the spectra correspond to the mono adduct formed as an intermediate during the reaction.

Example 5

Hydrogenation of Compound 3 to Form the Amino Derivative of N,N'-DMEDA (5)

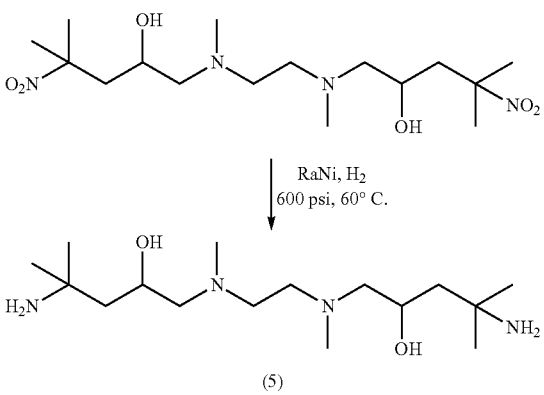

(5)

A 2-liter stirred Parr autoclave is charged with RaNi 3111 (19.8 g) and 200 mL of Methanol. The autoclave is sealed and purged via 3 cycles of pressurizing 50 psi N$_2$ followed by venting to 5 psi. This is also repeated using H$_2$ gas. After purging, the pressure of the autoclave is increased to 450 psi of H$_2$. The sealed reactor is then stirred at 600 rpm and the heater switched on at this time. The pressure is increased to 600 psi once the temperature of the autoclave reaches 60° C. At this point compound 3 (29 g, 0.076 mols) dissolved in 300 mL of Methanol is added into the autoclave containing RaNi at 7.0 mL/minute via a pump. After complete addition, the pump is switched off and the content of the autoclave stirred at 60° C. for 1 h, followed by stiffing at 45° C. for additional 0.5 h. The content in the autoclave is cooled to room temperature, the residual hydrogen is vented and the reactor opened. The product is filtered from the RaNi through suction filtration and excess methanol removed by rotary evaporator. This process results in 22.7 g (93%—crude) of deep red viscous oil. GC/MS analysis shows the Bis adduct 5 with [MH]$^+$ m/z 319 and retention time of 26.0 min. The VOC of the crude material is 12.4. The VOC is determined by heating the neat material at 110 degrees centigrade for 1 hour and calculating the weight loss. $^{13}$C NMR (CDCl$_3$): ∂ 32.1, 42.7, 50.9, 51.0, 55.4, 64.0 and 65.9 ppm. GC-MS analysis shows that in addition to the title bis product, the mono adduct and the hydrolysis product formed during the ring opening step are also present in the reduced (amine) form. The signals corresponding to these compounds are detected in the NMR also.

Example 6

Hydrogenation of Compound 4 to Form the Amino Derivative of Ethanolamine (6)

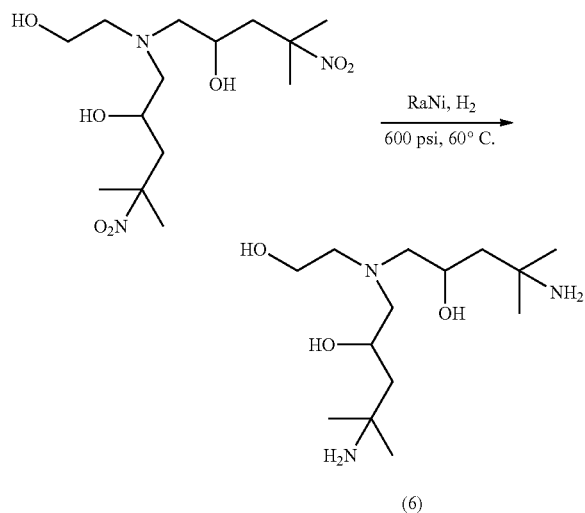

(6)

A 2-liter stirred Parr autoclave is charged with RaNi 3111 (27.8 g) and 200 mL of methanol. The autoclave is sealed and purged via 3 cycles of pressurizing 50 psi $N_2$ followed by venting to 5 psi. This is also repeated using $H_2$ gas. After purging, the pressure of the autoclave is increased to 450 psi of $H_2$. The sealed reactor is then stirred at 600 rpm and the heater switched on at this time. The pressure is increased to 600 psi once the temperature of the autoclave reaches 60° C. At this point compound 4 (34 g, 0.096 mols) dissolves in 300 mL of Methanol is added into the autoclave containing RaNi at 7.0 mL/minute via a pump. After complete addition, the pump is switched off and the content of the autoclave stirred at 60° C. for 1 h, followed by stirring at 45° C. for an additional 0.5 h. The content in the autoclave is cooled down to room temperature, the residual hydrogen is vented and the reactor opened. The product is filtered from the RaNi through suction filtration and excess methanol removed by rotary evaporator. This process results in 26.3 g (94%—crude) of deep red viscous oil. GC/MS analysis shows the Bis adduct 6 with $[MH]^+$ m/z 292 and retention time of 26.2 min. The VOC of the crude material is 14.2. The VOC is determined by heating the neat material at 110 degrees centigrade for 1 hour and calculating the weight loss. $^{13}$C NMR (CDCl$_3$): ∂ 32.4, 32.7, 44.8, 50.9, 62.4, 63.8, 66.0 and 67.5 ppm. GC-MS analysis shows that in addition to the titled bis product, the mono adduct and the hydrolysis product formed during the ring opening step are also present in the reduced (amine) form. The signals corresponding to these compounds are detected in the NMR also.

Example 7

Reaction of 2-(2-methyl-2-nitropropyl)oxirane with monomethylethanolamine (7)

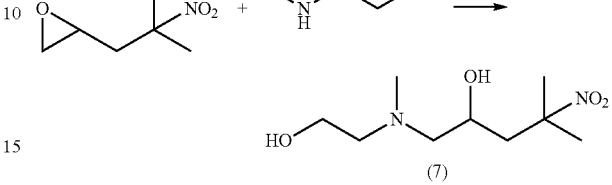

(7)

A one neck 50 mL round bottom flask equipped with a stir bar, condenser and nitrogen outlet is charged with 4.25 g (0.029 mols) of 2-(2-methyl-2-nitropropyl)oxirane and 2.87 mL (0.09 mols) of monomethylethanolamine. The reaction mixture is stirred at room temperature for 30 minutes followed by heating at 75° C. for 3 h. The yellow color oxirane turns to dark orange and the resulting product has high viscosity. GC analysis of the resulting mixture shows the starting materials are consumed during the 3 h reaction time. The major product present has retention time of 20.8 minutes and GC-MS CI confirms that the new peak is 1-((2-hydroxyethyl) (methyl)amino)-4-methyl-4-nitropentan-2-ol (7) with [M+H]=221.1. Hydrogenation reaction is done on the crude product without any further purification.

Hydrogenation of Compound (7) to Prepare 4-amino-1-((2-hydroxyethyl)(methyl)amino)-4-methylpentan-2-ol (8)

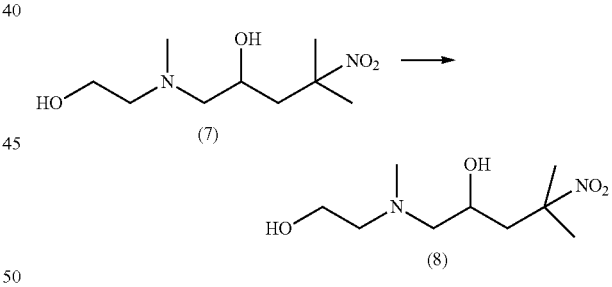

A 300 mL Parr autoclave is charged with methanol (150 mL), Raney Nickel catalyst (R-3111, 2.2 g wet weight) and compound (7) (6.2 g crude). The reactor is sealed, purged with nitrogen followed by purging with hydrogen and then brought up to 60° C. under 450 psi hydrogen pressure. When the autoclave temperature reaches 60° C., the reactor pressure is increased to approximately 630 psi. The reaction is stopped when no more hydrogen is consumed in the reaction. The entire reaction takes 2 h to reach completion. After cooling to room temperature, the reactor is vented and the catalyst isolated via vacuum filtration. The brown filtrate is stripped on a rotary evaporator (45-50° C./29-30" vacuum) to remove water/methanol. The above process provides 5.12 g of the crude mixture and has 90% by GC of the desired material present. GC-MS CI gives [M+H]=191 with retention time 17.5 min confirming the formation of 4-amino-1-((2-hydroxyethyl)(methyl)amino)-4-methylpentan-2-ol (8)

Example 8

Reaction of 2-(2-methyl-2-nitropropyl)oxirane with hexane-1,6-diamine to make (9)

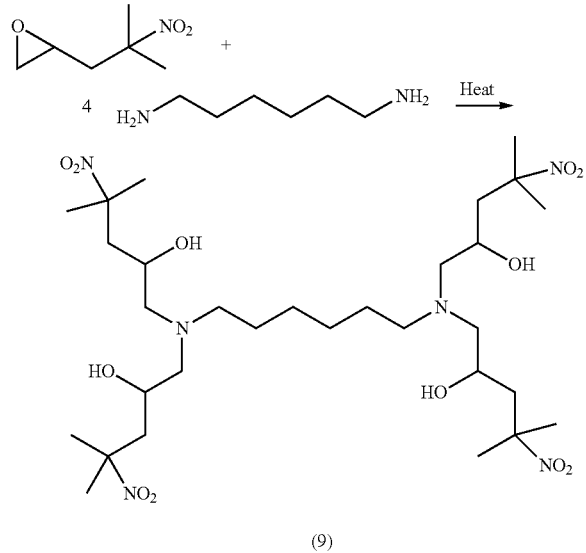

A one neck 50 mL round bottom flask equipped with a stir bar, condenser and nitrogen outlet is charged with 4.60 g (0.03 mols) of 2-(2-methyl-2-nitropropyl)oxirane and 0.85 g (0.007 mols) of hexane-1,6-diamine. The reaction mixture is stirred at room temperature for 30 minutes followed by heating at 80° C. for 8-10 h. The yellow color oxirane turns to dark brown and the resulting product has high viscosity. GC analysis of the resulting mixture shows the starting materials are consumed during the 8-10 h reaction time. The nitro amine products are too large to show up on the GC-MS and the reaction is deemed complete once the starting material peaks in the GC disappear. The resulting dark brown high viscous material is taken as-is to the hydrogenation step.

Hydrogenation of Compound (9) to Prepare Compound (10)

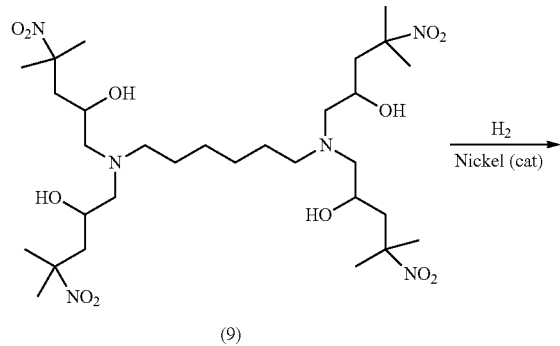

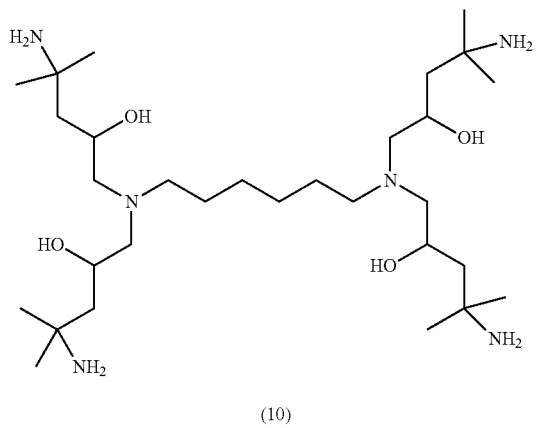

A 300 mL Parr autoclave is charged with methanol (150 mL), Raney Nickel catalyst (R-3111, 5.0 g wet weight) and compound (9) (5 g crude) dissolved in 50 mL MeOH. The reactor is sealed, purged with nitrogen followed by purging with hydrogen and then brought up to 60° C. under 450 psi hydrogen pressure. When the temperature reaches 60° C., the reactor pressure is increased to approximately 750 psi. The reaction is stopped when no more hydrogen is consumed in the reaction. The entire reaction takes 2-2.5 h to get to completion. After cooling to room temperature, the reactor is vented, opened and the catalyst isolated via vacuum filtration. The brown filtrate is stripped on a rotary evaporator (50-55° C./28-29" vacuum) to remove water/methanol. The above process yields 3.8 g of the crude mixture. Therefore, the compound (10) is identified by LC/MS with [M+H]=577. The main impurities in the sample are the ones carried over during the synthesis of 2-(2-methyl-2-nitropropyl)oxirane.

Example 9

Preparation of 1-allyl-1-nitrocyclohexane

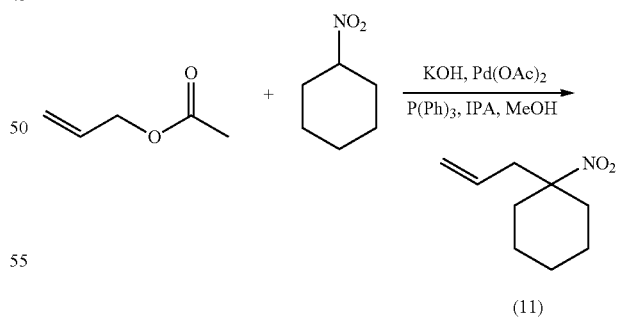

A 3 neck 2 L round bottom flask equipped with dropping funnel, temperature controller, nitrogen outlet, stir bar and condenser is charged with 71 g (1.27 mols) of potassium hydroxide (KOH), 300 mL of methanol and 300 mL of isopropanol. The addition takes place at room temperature, however, while the base is dissolving in the solvent there is approximately 30° C. increase in temperature. The base solution is allowed to stir under nitrogen for 20 minutes. During this time, the temperature of the flask goes down to 44.7° C. To the above base solution, 156 g of nitrocyclohexane ("NCy-Hex") (1.16 mols) is added slowly with vigorous stirring. The mixture stirred for 10 minutes, and palladium acetate (0.56 mmol)/triphenyl phosphine (1.7 mmol) added as catalyst. The resulting yellow solution stirred under nitrogen for another 5 minutes and 139.5 mL (1.06 mols) of allyl acetate added drop-wise to the mixture via the dropping funnel. During the addition of the acetate, the reaction mixture turns brown but transparent. During the addition, the temperature rises. At this point, heat is switched on and the mixture stirred for 8 h at 55° C. followed by overnight stiffing at room temperature. The next day the mixture is heated again to 55° C. followed by room temperature stirring overnight. After the reaction is complete, the contents of the flask are poured into a separatory funnel containing 600 mL of water. The organic layer is extracted with pentane (3×200 mL) and dried under MgSO$_4$. Excess solvent is removed under a rotary evaporator and 167 g (93.5%) of deep brown solution of the desired 1-allyl-1-nitrocyclohexane (11) obtained at 90.7% purity. GC/MS analysis shows [MH]$^+$ m/z 123.

Example 10

Preparation of 2-((1-nitrocyclohexyl)methyl)oxirane (12)

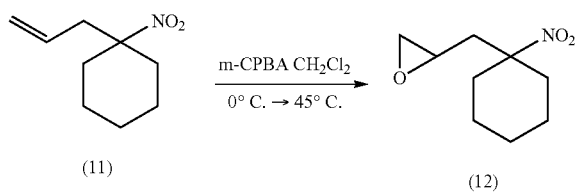

A 1 neck 500 mL round bottom flask equipped with dropping funnel, temperature controller, nitrogen outlet, stir bar and condenser is charged with approximately 37 g of mCPBA (72% pure, 0.15 mols) and 100 mL of CH$_2$Cl$_2$. The reaction slurry is warmed to dissolve all the solids in CH$_2$Cl$_2$. Once a clear solution is obtained, 20 g (0.12 mols) of 1-allyl-1-nitrocyclohexane (11) is added slowly. After complete addition, the reaction is refluxed for 2 hrs and stirred for 48 h at room temperature. The progress of the reaction is monitored by GC. After the duration of almost 50 h, the composition of the epoxide in the reaction mixture is approximately 38.5%. Solid mCPBA that crashes out of solution is removed by gravity filtration. The organic layer is washed with 10% Na$_2$CO$_3$ (3×30 mL) followed by brine (3×30 mL). The organic layer is dried under MgSO$_4$ and excess solvent stripped off under rotary evaporator. This affords 11.8 g of crude material. The retention time of the epoxide on the GC is 18.3 minutes. The presence of epoxide is confirmed by GC-MS CI. The parent ion is not detected due to the labile nature of NO2 groups. However, the fragment minus the NO$_2$ is observed. CI GC/MS, [C$_9$H$_{15}$O]$^+$=139.

Example 11

Preparation of 1-((2-hydroxyethyl)(methyl)amino)-3-(1-nitrocyclohexyl)propan-2-ol (13)

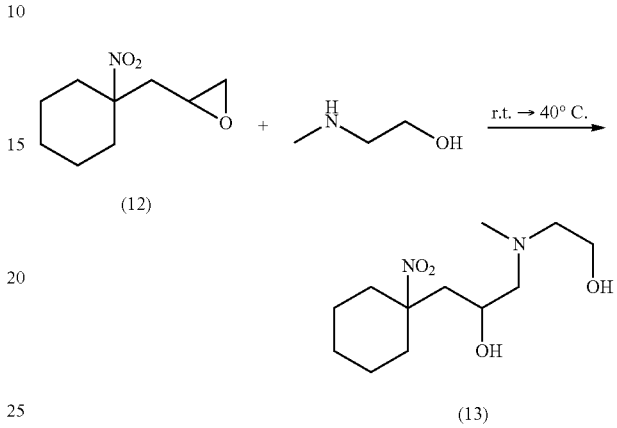

A one neck 100 mL round bottom flask equipped with a stir bar, condenser and nitrogen outlet is charged with 3.24 g (34.6% purity, 0.018 mols) of 24(1-nitrocyclohexyl)methyl)oxirane and 1.31 g (0.018 mols) of monomethylethanolamine. The reaction mixture is stirred at room temperature for 30 minutes followed by heating at 40° C. for 1.5 h. The yellow color oxirane turns to dark orange and the resulting product has high viscosity. GC of the reaction mixture after this time still shows the presence of the epoxide. At this point, 0.7 mL (0.65 g) of additional monomethylethanolamine is added and stirred for additional 1.5 h at 40° C. and overnight at room temperature. GC analysis of the resulting mixture shows the nitro epoxide (12) is fully consumed. At this point, the reaction is deemed complete. Compound (13), 1-((2-hydroxyethyl)(methyl)amino)-3-(1-nitrocyclohexyl)propan-2-ol was identified by LC/MS with [M+H]=261.17. The product mixture from the epoxy ring opening step is used as-is for the hydrogenation step.

Example 12

Preparation of 1-(1-aminocyclohexyl)-3-((2 hydroxyethyl)(methyl)amino)propan-2-ol (14)

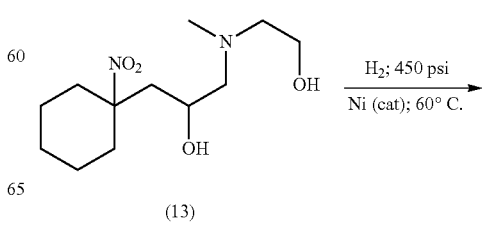

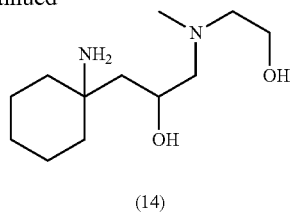

(14)

A 300 mL Parr autoclave is charged with methanol (100 mL), Raney Nickel catalyst (R-3111, 6.8 g wet weight) and compound (13) (20.8 g crude) dissolved in 100 mL MeOH. The reactor is sealed, purged with nitrogen followed by purging with hydrogen and then brought up to 60° C. under 400 psi hydrogen pressure. When the temperature reaches 60° C., the reactor pressure is increased to approximately 450 psi. The reaction is stopped when no more hydrogen is consumed in the reaction. The entire reaction takes 1-1.5 h to reach completion. After cooling to room temperature, the reactor is vented, opened and the catalyst isolated via vacuum filtration. The brown filtrate is stripped on a rotary evaporator (50-55° C./28-29" vacuum) to remove water/methanol. The above process provides 6.4 g of the crude mixture. The desired material, compound (14) is eluted in GC-MS EI at retention time of 22.7 minutes, however the molecular ion peak cannot not be seen due to fragmentation in the GC. The presence of 1-(1-aminocyclohexyl)-3-((2 hydroxyethyl) (methyl)amino)propan-2-ol (14) is identified by LC/MS with [M+H]=231.20.

Example 13

Titration for pKa Values

Aqueous titrations are done on automatic titrator (Metrohm Titroprocessor 726, with Dosimat 685 and stirrer 728) with 0.1N HCl titrant, with a potentiometric probe. The titrator determines pKa from the pH vs. titrant volume curve. The pKa is equal to the pH at the titrant volume halfway to the first neutralization endpoint, corresponding to bis-molecule. Endpoints are the inflection points on the curve. The pKa values recorded for compounds 5 and 6 ranged from 9.8 to 10.3.

Example 14

Efficacy as a Neutralizing, Co-Dispersing Amine in a Paint Formulation

Inventive compounds 5 and 6 are tested as neutralizing and co-dispersing amines and compared relative to a commercial neutralizer in an aqueous based, latex semi-gloss formulation. The comparative neutralizer is 2-amino-2-methyl-1-propanol.

The paint formulation in which the compounds are tested is latex based semi-gloss material containing:

Pigments such as titanium dioxide (e.g., TIPURE® R942 from DuPont) and ground calcium carbonate (e.g., OMYAC-ARB® UF from Omya, Inc.) (total of both pigments 20-25%).

Binder such as UCAR™ Latex 379 and 6030 from The Dow Chemical Company (total of both binders 40-45%).

Thickeners and rheology modifiers such as hydroxyethyl-cellulose (e.g., CELLOSIZE™ HEC from Dow) and solvent-free, non-ionic associative thickening agent/hydrophobically modified polyethylene oxide urethane -HEUR (ACRYSOL™ RM-5000 from Rohm and Haas) (total of both thickener (3-5%).

Neutralizer or amine such as 2-amino-2-methyl-1-propanol (comparative), or Compound 5 or 6 (inventive) were included in the paint formulation either as equal weight or equal molar (see Table below). The amount by weight varied from approximately 2-7 gms per kg of total paint formulation.

The pH, VOC, film opacity, and gloss of the formulations containing the various tested compounds are determined as follows:

pH Measurements. The formulation pH is measured using a Fisher Scientific Accumet 15 pH meter, equipped with a ThermoElectron Orion 9203BN combination pH electrode. Commercial pH buffers are used to calibrate the equipment before each use. The reported values are the average of three separate reading on each formulation, the probe is cleaned with DI water between each measurement.

Volatile Organic Content (VOC). VOC is measure following modified EPA Method 24. The neat amines are weighed in a pan and kept in an oven for 1 h at 105-110° C. The percent weight loss is measured and is reported as the VOC, corrected for the water content in the sample which can be measured by Karl Fisher Titration.

Coating Optical Properties (Opacity and Gloss). The opacity, gloss at 20, 60, and 85° and color of the dried films is measured using an automated color/gloss/thickness robot based on a Symyx XCM module. The color is measured using an Ocean Optics ISP-REF integrating sphere with a 0.4" sampling aperture connected by a fiber optic cable to an Ocean Optics USB 4000 Spectrometer. Measurements are performed with D65 illumination. This apparatus is located on the left arm of a Symyx Core Module Robot which enables the colorimeter to be moved onto the sample in multiple locations. For this study measurements are done on three separate areas on both the black and white parts of each Leneta paper. The gloss is measured using a BYK micro-Tri-gloss Meter. This instrument is attached to the right arm of the Symyx Core Module Robot, along with a plate gripper used to move the samples from the BenchCel sample hotel to the deck of the Module. Gloss is measured in three different spots on the coatings over both the white and black parts of the Leneta paper.

The data comparing compounds of the invention to 2-amino-2-methyl-1-propanol are shown in Table 3.

TABLE 3

|  | Comparative[1] | Compound 5[2] | Compound 6[2] |
| --- | --- | --- | --- |
| pH | 9.4 | 10.2 | 10.0 |
| VOC ((%)* | 100 | 12.4 | 14.2 |
| Opacity (equal molar) | 98 | 96.6 | 97.7 |
| Gloss (equal molar) | 70.4 | 70.9 | 78.2 |
| Opacity (equal weight) | 97.4 | 97 | 97.5 |
| Gloss (equal weight) | 74.4 | 72.8 | 70.0 |

[1]2-Amino-2-methyl-1-propanol.
[2]Compound of the invention.
*VOC of neat amine only As can be seen from the results, inventive Compounds 5 and 6 perform comparably to the commercial material, 2-amino-2-methyl-1-propanol, achieving good co-dispersion of the pigment (as represented by the particle size analysis) which translates into good film opacity and gloss measurements. Advantageously, the inventive compounds provide these comparable results at a considerably lower VOC contribution than the commercial material. Further advantageously, the inventive compounds have a low odor in low VOC paint formulations.

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A compound of formula I:

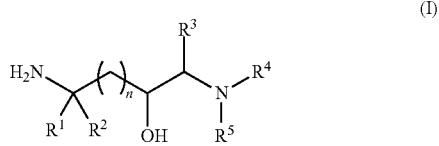

(I)

or a salt thereof, wherein n at all occurrences is 1;
$R^1$ is H or $C_1$-$C_{10}$ alkyl, $R^2$ is $C_1$-$C_{10}$ alkyl, or $R^1$ and $R^2$, together with the carbon to which they are attached, form a $C_3$-$C_{12}$ cycloalkyl ring optionally substituted with $C_1$-$C_6$ alkyl;
$R^3$ is H, $C_1$-$C_{10}$ alkyl, or phenyl;
$R^4$ is H, $C_1$-$C_{10}$ alkyl optionally substituted with hydroxy, $-(C(R^6)(R^7))_m-N(R^8)(R^9)$, or Y, wherein m is an integer from 1 to 6, and $R^6$ and $R^7$ are independently H or $C_1$-$C_{10}$ alkyl;
$R^5$, $R^8$, and $R^9$ are independently H, $C_1$-$C_{10}$ alkyl optionally substituted with hydroxy, or Y; and
Y is a group of formula:

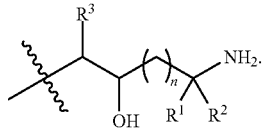

2. A compound according to claim 1 wherein:
$R^4=-(C(R^6)(R^7))_m-N(R^8)(R^9)$;
$R^5=R^8=$H or $C_1$-$C_{10}$ alkyl; and
$R^9=$H.

3. A compound according to claim 1 wherein:
$R^4=-(C(R^6)(R^7))_m-N(R^8)(R^9)$;
$R^5=R^8=$H or $C_1$-$C_{10}$ alkyl; and
$R^9=$Y.

4. A compound according to claim 1 wherein:
$R^4=-(C(R^6)(R^7))_m-N(R^8)(R^9)$;
$R^5=$H or $C_1$-$C_{10}$ alkyl; and
$R^8=R^9=$Y.

5. A compound according to claim 1 wherein:
$R^4=-(C(R^6)(R^7))_m-N(R^8)(R^9)$; and
$R^5=R^8=R^9=$Y.

6. A compound according to claim 1 wherein:
$R^4$ =H or $C_1$-$C_{10}$ alkyl optionally substituted with hydroxy; and
$R^5$ =$C_1$-$C_{10}$ alkyl substituted with hydroxy.

7. A compound according to claim 1 wherein:
$R^4$=Y; and
$R^5$=$C_1$-$C_{10}$ alkyl substituted with hydroxy.

8. A compound according to according to claim 1 wherein $R^4=R^5=$Y.

9. A compound according to claim 1 selected from the group consisting of:
1,1'-(ethane-1,2-diylbis(methylazanediyl))bis(4-amino-4-methylpentan-2-ol); 1,1'-(2-hydroxyethylazanediyl)bis (4-amino-4-methylpentan-2-ol); 3,3'-(ethane-1,2-diyl-bis(methylazanediyl))bis(1-(1-aminocyclohexyl) propan-2-ol); 1-(1-aminocyclohexyl)-3-((2-hydroxyethyl)(methyl)amino)propan-2-ol; 4-amino-1-((2-hydroxyethyl)(methyl)amino)-4-methylpentan-2-ol; 2,2'-(3-(1-aminocyclohexyl)-2-hydroxypropylazanediyl) diethanol; 2,2'(4-amino-2-hydroxy-4-methylpentylazanediyl)diethanol; 4-amino-1-(2-hydroxyethylamino)-4-methylpentan-2-ol; 4-amino-4-methyl-1-(methyl(2-(methylamino)ethyl) amino)pentan-2-ol; 4-amino-1-(1-hydroxy-2-methyl-propan-2-ylamino)-4-methylpentan-2-ol; 1,1',1'',1'''-(hexane-1,6-diylbis(azanetriyl))tetrakis(4-amino-4-methylpentan-2-ol); and mixtures of two or more thereof.

10. An aqueous based paint or coating comprising a neutralizing agent, a binder, a carrier, and a pigment, wherein the neutralizing agent is a compound according to claim 1.

11. The aqueous based paint or coating according to claim 10 further comprising one or more additional ingredients selected from: leveling agents, surfactants, thickeners, rheology modifiers, co-solvents, corrosion inhibitors, defoamers, co-dispersants, additional aminoalcohol compounds, and biocides.

12. A process for making a compound according to claim 1 the process comprising:
(a) combining a nitroalkyloxirane compound of formula III:

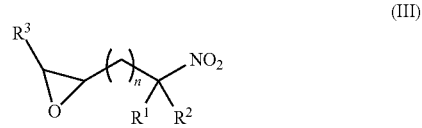

(III)

wherein n at all occurrences is 1; $R^1$ is H or $C_1$-$C_{10}$ alkyl, $R^2$ is $C_1$-$C_{10}$ alkyl, or $R^1$ and $R^2$, together with the carbon to which they are attached, from a $C_3$-$C_{12}$ cycloalkyl ring optionally substituted with $C_1$-$C_6$ alkyl; and $R^3$ is H, $C_1$-$C_{10}$ alkyl or phenyl;
with an amine of formula $HNR^{10}R^{11}$, wherein $R^{11}$ is H, or $C_1$-$C_{10}$ alkyl optionally substituted with hydroxyl; and $R^{10}$ is H, $C_1$-$C_{10}$ alkyl optionally substituted with hydroxy, or $-(C(R^6)(R^7))_m-N(R^{12})(R^{13})$, wherein m is an integer from 1 to 6, and $R^6$ and $R^7$ are independently H or $C_1$-$C_{10}$ alkyl, and $R^{12}$ and $R^{13}$ are independently H or $C_1$-$C_{10}$ alkyl optionally substituted with hydroxy
to form a compound of formula II:

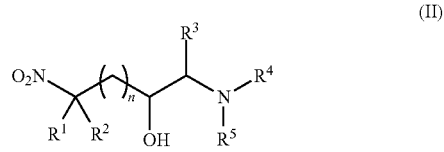

(II)

wherein $R^4$ is H $C_1$-$C_{10}$ alkyl optionally substituted with hydroxy, $-(C(R^6)(R^7))_m-N(R^8)(R^9)$, or Y'; $R^5$, $R^8$, and $R^9$ are independently H, $C_1$-$C_{10}$ alkyl optionally substituted with hydroxy, or Y'; and Y' is a group of formula:

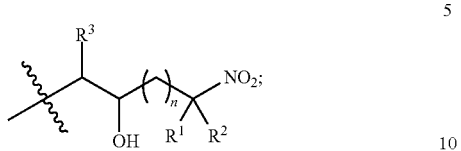

and
(b) contacting the product of step (a) with a reducing agent capable of reducing nitro groups.

13. The process according to claim 12 wherein the nitroalkyloxirane compound of formula III is used at a molar excess relative to the amine.

14. A method for reducing a volatile organic compound content of an aqueous based paint or coating that contains a neutralizing agent, a binder, a carrier, and a pigment, the method comprising using as the neutralizing agent an effective amount of a compound according to claim 1.

* * * * *